US009045855B2

(12) United States Patent
Fujimori et al.

(10) Patent No.: US 9,045,855 B2
(45) Date of Patent: Jun. 2, 2015

(54) ANTI-VIRAL MEMBER

(75) Inventors: Yoshie Fujimori, Tokyo (JP); Tsuruo Nakayama, Tokyo (JP); Yoko Fukui, Tokyo (JP)

(73) Assignee: NBC Meshtec, Inc., Tokyo (JP)

( * ) Notice: Subject to any disclaimer, the term of this patent is extended or adjusted under 35 U.S.C. 154(b) by 732 days.

(21) Appl. No.: 13/142,118

(22) PCT Filed: Dec. 28, 2009

(86) PCT No.: PCT/JP2009/007364
§ 371 (c)(1),
(2), (4) Date: Jun. 24, 2011

(87) PCT Pub. No.: WO2010/073738
PCT Pub. Date: Jul. 1, 2010

(65) Prior Publication Data
US 2011/0262513 A1    Oct. 27, 2011

(30) Foreign Application Priority Data

Dec. 26, 2008   (JP) ................. 2008-334151

(51) Int. Cl.
*A01N 25/08*    (2006.01)
*D06M 11/13*    (2006.01)
(Continued)

(52) U.S. Cl.
CPC ............ *D06M 11/13* (2013.01); *A61K 39/42* (2013.01); *A01N 25/34* (2013.01); *A01N 59/20* (2013.01); *D06M 11/42* (2013.01); *D06M 11/53* (2013.01);
(Continued)

(58) Field of Classification Search
CPC ..................................... A61K 39/42
See application file for complete search history.

(56) References Cited

U.S. PATENT DOCUMENTS 5,468,738 A    11/1995   Okabayashi et al.
6,840,310 B2 *  1/2005   Tonosaki et al. ......... 165/104.21
(Continued)

FOREIGN PATENT DOCUMENTS

EP    1 972 437      9/2008
JP    2006-061320   3/2006

OTHER PUBLICATIONS

A machine translation of JP 06-092808-A , Feb. 2014.*
(Continued)

*Primary Examiner* — Paul Dickinson
(74) *Attorney, Agent, or Firm* — Wenderoth, Lind & Ponack, L.L.P.

(57) ABSTRACT

Disclosed is an anti-viral member which can inactivate a virus. Specifically disclosed is an anti-viral member which is characterized by comprising a base material, univalent copper compound microparticles, and inorganic microparticles which are provided for the purpose of retaining the univalent copper compound microparticles on the base material and each of which has a silane monomer bound to the surface thereof via a chemical bond, wherein the inorganic microparticles are bound to one another via chemical bonds formed between the silane monomers provided on the surfaces thereof, and each of the inorganic microparticles is bound to the base material via a chemical bond between the silane monomer and the base material to form spaces in which the univalent copper compound microparticles are to be retained. The anti-viral member has an extremely high anti-viral activity compared to those achieved by the conventional binder immobilization techniques, and is applicable to various materials or various products to which the materials are applied.

16 Claims, 1 Drawing Sheet

(51) Int. Cl.
| | |
|---|---|
| *A61K 39/42* | (2006.01) |
| *A01N 25/34* | (2006.01) |
| *A01N 59/20* | (2006.01) |
| *D06M 11/42* | (2006.01) |
| *D06M 11/53* | (2006.01) |
| *D06M 11/67* | (2006.01) |
| *D06M 13/188* | (2006.01) |
| *D06M 13/513* | (2006.01) |
| *D06M 16/00* | (2006.01) |
| *D06M 23/08* | (2006.01) |

(52) U.S. Cl.
CPC ............ *D06M 11/67* (2013.01); *D06M 13/188* (2013.01); *D06M 13/513* (2013.01); *D06M 16/00* (2013.01); *D06M 23/08* (2013.01)

(56) References Cited

U.S. PATENT DOCUMENTS

2006/0208390 A1* 9/2006 Charbonneaux et al. ..... 264/165
2007/0184079 A1 8/2007 Gabbay

OTHER PUBLICATIONS

International Search Report issued Mar. 16, 2010 in International (PCT) Application No. PCT/JP2009/007364.
English Abstract of JP 2006-188499 published Jul. 20, 2006.
English Abstract of WO 2005/083171 published Sep. 9, 2005.
English Abstract of JP 2008-138323 published Jun. 19, 2008.
English Abstract of JP 06-092808 published Apr. 5, 1994.
English Abstract of JP 08-048605 published Feb. 20, 1996.
English Abstract of JP 2000-070673 published Mar. 7, 2000.
English Abstract of JP 2002-339243 published Nov. 27, 2002.
English Abstract of JP 2009-286002 published Dec. 10, 2009.
Extended European Search Report dated May 23, 2014 issued in corresponding European Patent Application No. 09834544.0.
Borkow, Gadi et al., "Putting copper into action: copper-impregnated products with potent biocidal activities", The FASEB Journal, Published online Sep. 2, 2014, vol. FJ Express, pp. 1-19.

* cited by examiner

ANTI-VIRAL MEMBER

TECHNICAL FIELD

The present invention relates to an antiviral member that exhibits a high inactivation effect against various viruses regardless of the presence of an envelope.

BACKGROUND ART

Recently, deaths have been reported that are caused by viral infections such as SARS (severe acute respiratory syndrome), norovirus, and avian influenza. In addition, currently, due to developments in transportation and the sudden mutations of viruses, the world faces the risk of a "pandemic" in which viral infection spreads throughout the world, and thus there is an urgent need for countermeasures. To deal with such a situation, although the development of antiviral agents based on a vaccine is being hastened, due to the specificity of vaccines, the infections that can be prevented are limited to specific viruses. Further, at hospitals and medical clinics, nosocomial infection caused by contagious infection of MRSA (methicillin-resistant *Staphylococcus aureus*) brought into the hospital by a carrier or an infected person or a species mutated from *Staphylococcus aureus* to MRSA due to antibiotic administration from a patient directly or via healthcare staff or an environment that includes used articles such as medical coats, pajamas, and sheets, and facilities such as walls and air conditioning units to other patients and healthcare staff is also becoming a serious problem in society. Therefore, there is a strong need for the development of an antiviral member that can exhibit an effective antibacterial and antiviral effect against various viruses and bacteria.

Viruses can be classified into those that are surrounded by a membrane called an "envelope" that includes lipids, and those that do not have an envelope. Since an envelope is largely made up of lipids, envelopes can be easily destroyed by treating with ethanol, an organic solvent, soap and the like. Consequently, although viruses that have an envelope are generally easy to inactivate, viruses that do not have an envelope are said to have a strong resistance against such treatment agents.

Inorganic antiviral agents, which have a wider action than organic agents, have been proposed as an antiviral agent for resolving these problems. For example, cloth containing an antibacterial coloring agent and divalent copper ions has been proposed as an article that inactivates (reduces the infectiousness of a virus or deactivates a virus) the influenza virus (Patent Document 1). Further, antiviral fibers containing a copper compound in fibers including a carboxyl group have also been proposed (Patent Document 2). In addition, very fine copper fibers produced by cold working have been proposed as an article that inactivates the avian influenza virus (Patent Document 3).

[Patent Document 1] Japanese Patent Application Laid-Open No. 2006-188499

[Patent Document 2] International Publication No. 2005/083171 Pamphlet

[Patent Document 3] Japanese Patent Application Laid-Open No. 2008-138323

DISCLOSURE OF THE INVENTION

Problems to be Solved by the Invention

However, with the method in which divalent copper ions are used, it is necessary to stabilize the copper ions by mixing with another substance, so that the ratio of the copper ions in the resultant composition is limited. In other words, it is necessary to include a stabilizing agent for the divalent copper ions. Consequently, the antiviral member has little design freedom. Further, since there has to be a salt in addition to the carboxyl group for the case in which a copper compound is included in fibers containing a carboxyl group, the supported amount of the copper compound is limited, thus preventing a sufficient antiviral performance from being exhibited. In addition, in the case in which metal copper is used, contamination such as a natural oxide film adheres to the metal copper surface, so that the effects of the antiviral activity drastically deteriorate. Consequently, there is the problem that special cleaning is constantly necessary in order to maintain the antiviral activity, which means that maintenance takes time.

Accordingly, to resolve the above problems, the present invention provides an antiviral member that can inactivate a virus, and a product using this member.

Means for Solving the Problems

More specifically, a first aspect of the invention is an antiviral member, comprising a substrate, univalent copper compound particles, and a group of inorganic particles which are for supporting the univalent copper compound particles on the substrate and which have a silane monomer chemically bonded to a surface thereof, wherein the inorganic particles having the silane monomer on the surface thereof are bonded to each other via chemical bonds formed between the silane monomers provided on the surface of the inorganic particles, and the group of inorganic particles are bonded to the substrate due to the chemical bonds between the silane monomers on the surface of the inorganic particles and the substrate, whereby the group of inorganic particles forms spaces for supporting the univalent copper compound particles.

Further, a second aspect of the invention is an antiviral member, comprising coating a substrate with a slurry in which inorganic particles having a silane monomer, which has an unsaturated bonding site or a reactive functional group, chemically bonded to a surface thereof and univalent copper compound particles are dispersed, making the inorganic particles having the silane monomer chemically bonded to the surface thereof be bonded to each other by chemical bonds that are formed between the silane monomers on the surface of the inorganic particles, and making the group of inorganic particles be bonded to the substrate by chemical bonds formed between the unsaturated bonding site or the reactive functional group of the silane monomers and the substrate surface, whereby spaces for supporting the univalent copper compound particles is formed, and supporting the univalent copper compound particles in the space.

In addition, a third aspect of the invention is the antiviral member according to the first or second aspects of the invention, wherein the chemical bonds between the silane monomers and the inorganic particles are covalent bonds formed by dehydration condensation, the chemical bonds among the silane monomers are covalent bonds formed by radical polymerization, and the chemical bonds between the silane monomers and the substrate are covalent bonds formed by graft polymerization.

Moreover, a fourth aspect of the invention is the antiviral member according to the third aspect of the invention, wherein the radical polymerization is radiation-induced radical polymerization, and the graft polymerization is radiation-induced graft polymerization.

Still further, a fifth aspect of the invention is the antiviral member according to any one of the first to fourth aspects of the invention, wherein the univalent copper compound particles are bonded to the inorganic particles via a binder component which is a monomer, an oligomer, or a mixture thereof.

Still further, a sixth aspect of the invention is the antiviral member according to any one of the first to fifth aspects of the invention, wherein the univalent copper compound particles are formed of a chloride, an acetate, a sulfide, an iodide, a bromide, a peroxide, an oxide, a hydroxide, a cyanide, a thiocyanate or a mixture thereof.

Still further, a seventh aspect of the invention is the antiviral member according to the sixth aspect of the invention, wherein the univalent copper compound particles are formed of at least one kind selected from the group consisting of CuCl, $CuCH_3COO$, CuI, CuBr, $Cu_2O$, CuOH, $Cu_2S$, CuCN, and CuSCN.

Still further, an eighth aspect of the invention is the antiviral member according to any one of the first to seventh aspects of the invention, wherein a content of the univalent copper compound particles is, with respect to a total solid content on the substrate, 0.1 mass % to 60 mass %.

Still further, a ninth aspect of the invention is the antiviral member according to any one of the first to eighth aspects of the invention, wherein the substrate is a fibrous structure. As the fibrous structure, a known structure may be used. Examples thereof include an air-conditioning filter, a net, an insect protection net, a mosquito net, bedding, clothing, and a mask. Further, the substrate used in the present invention may be, for example, a film or a sheet. In addition, the substrate used in the present invention may be, for example, a molded body such as a panel, a construction material, and an interior material.

Advantages of the Invention

According to the present invention, an antiviral member that, even when various viruses such as viruses that are surrounded by a membrane called an "envelope" that includes lipids or viruses that do not have an envelope are adhered, can inactivate the adhered virus more easily than conventionally, and a product that is formed using this antiviral member can be provided.

BEST MODE FOR CARRYING OUT THE INVENTION

Next, the antiviral member according to the present embodiment will be described in detail using a drawing.

Figure 1:
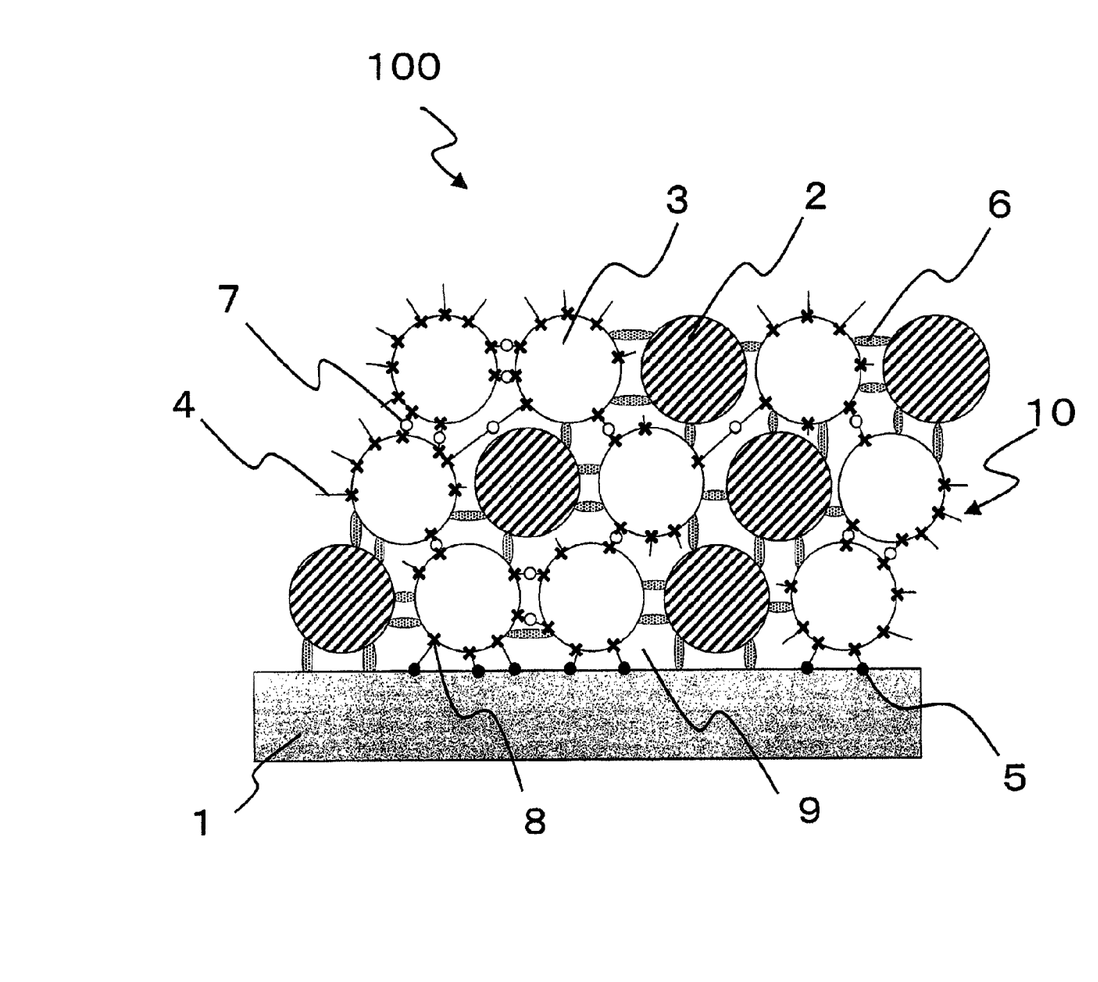
FIG. 1 is a schematic diagram of the antiviral member according to the present embodiment.

FIG. 1 is an expanded diagram schematically illustrating a portion of a cross-section of an antiviral member 100 according to the present invention. In the antiviral member 100 according to the present embodiment, univalent copper compound particles 2 that exhibit an antiviral activity are supported on a substrate 1 by a group 10 of inorganic particles 3 to which silane monomers 4 are bonded by a chemical bond 8 (covalent bond) formed by a dehydration condensation reaction.

Although currently the inactivation mechanism of viruses is not completely clear, it is believed that if a univalent copper compound comes into contact with moisture in the air, part of the copper compound tries to form the more stable divalent copper ion, thereby releasing an electron. These released electrons are thought to affect electrical charge of the surface of a virus adhered to the antiviral member 100 according to the present embodiment, DNA of the virus or the like, whereby the virus is inactivated.

The antiviral member 100 according to the present embodiment exhibits an antiviral activity even if the univalent copper compound particles 2, which are the active component, are not mixed with a stabilizing agent and the like. More specifically, the antiviral member 100 according to the present embodiment can be designed with a greater degree of freedom than a conventional antiviral composition that uses divalent copper ions and the like.

Further, in the antiviral member 100 according to the present embodiment, the univalent copper compound particles 2, which are the active component, are supported in a space 9 formed by the group 10 of inorganic particles 3 fixed to the substrate 1 without being covered with a binder or the like. Consequently, the particle density of the univalent copper compound particles 2 on the substrate 1 can be increased, and the probability of a virus adhered to the surface of the antiviral member 100 coming into contact with the univalent copper compound particles 2 can be increased. In addition, the efficiency of antiviral activity is much higher than for a conventional antiviral member, in which an antiviral agent buried under a binder cannot sufficiently exhibit the activity. Moreover, unlike metal copper, whose antiviral activity deteriorates due to an oxide film being formed on the surface unless special cleaning is performed, virus inactivation activity can be maintained for a longer duration even without performing special cleaning and the like.

Although the type of the univalent copper compound particles 2, which are the active component, is not limited, preferred is a chloride, an acetate, a sulfide, an iodide, a bromide, a peroxide, an oxide, a hydroxide, a cyanide, a thiocyanate or a mixture thereof. Among these, it is substantially more preferred that the univalent copper compound particles 2 are at least one kind selected from the group consisting of CuCl, $CuCH_3COO$, CuI, CuBr, $Cu_2O$, CuOH, $Cu_2S$, CuCN, and CuSCN.

Further, although the size of the included univalent copper compound particles 2 is not especially limited, it is preferred that they have an average particle size of 500 μm or less. If the average particle size is more than 500 μm, the particle surface area per unit mass decreases, which means that the antiviral effect is less than when the average particle size is 500 μm or less. In addition, compared with when the average particle size is 500 μm or less, the inherent texture of the substrate 1 surface is harmed, and the fixing strength to the substrate 1 weakens, so that the univalent copper compound particles 2 tend to peel and fall from the substrate 1 due to frictional force. Especially, for a fibrous structure such as a filter, a net, and clothing, or for a sheet or a film, the univalent copper compound particles 2 fixed to the surface of the substrate 1, such as a fiber or a sheet, can peel off due to the usage environment or the passage of time. Therefore, considering the adhesive strength of the film, it is preferred that the average particle size of the univalent copper compound particles 2 is 10 nm or more to 1 μm or less.

For strength reinforcement, the univalent copper compound particles 2 may optionally be bonded to the inorganic particles 3 via a binder component 6 formed from a monomer, an oligomer, or a mixture thereof that acts as a reinforcing agent.

In other words, the antiviral member 100 according to the present embodiment may include a binder component 6 formed from a monomer, an oligomer, or a mixture thereof, that bonds the univalent copper compound particles 2 and the inorganic particles 3 in a state that maintains the antiviral activity of the univalent copper compound particles 2 (state in which at least part of the surface of the univalent copper compound particles 2 is exposed to the outside).

Further, in addition to the univalent copper compound particles 2 that are supported in the space 9 formed by the group 10 of inorganic particles 3 being fixed to the substrate 1, the antiviral member 100 may also include univalent copper compound particles 2 which are fixed to the surface of the antiviral member 100 by being bonded to the inorganic particles 3 via the binder component 6, as illustrated in FIG. 1.

Still further, as illustrated in FIG. 1, in addition to bonding the univalent copper compound particles 2 and the inorganic particles 3, the binder component 6 may also bond the univalent copper compound particles 2 and the substrate 1, bond the univalent copper compound particles 2 to each other, and bond the inorganic particles 3 to each other.

The amount of the binder component 6 may be appropriately set in a range in which performance as a binder is exhibited, and the antiviral activity of the univalent copper compound particles 2 is maintained.

Further, in the present embodiment, concerning the binder component 6 as below-mentioned examples, although the binder component 6 forms a covalent bond 8 formed by a dehydration condensation reaction to bond to the univalent copper compound particles 2, the inorganic particles 3, and the substrate 1, the binder component 6 is not limited to this, and may be bonded or adsorbed in some other manner.

If the binder component 6 is a monomer, examples thereof may include a monomer having a reactive functional group, such as a vinyl group, an acryloyl group, an amino group, an amide group, an isocyanate group, an epoxy group, a carboxyl group, a carbonyl group, a hydroxyl group, and a silanol group. Further examples include monofunctional, bifunctional, and polyfunctional vinyl monomers, such as acrylate, methyl methacrylate, ethyl acrylate, n-butyl acrylate, 2-hydroxyethyl acrylate, methyl methacrylate, 2-hydroxyethyl acrylate, acrylamide, methacrylamide, acrylonitrile, vinyl acetate, ethylene, styrene, propylene, butadiene, vinyl chloride, formaldehyde, itaconic acid, methyl acrylate, trimethylolpropane triacrylate, and pentaerythritol triacrylate. One kind or a mixture of two or more kinds of these monomers may be used.

If the binder component 6 is an oligomer, examples thereof may include an unsaturated polyester, an unsaturated acrylic, an epoxy acrylate, a urethane acrylate, a polyester acrylate, a polyether acrylate, a polybutadiene acrylate, a silicone acrylate, maleimide, a polyene/polythiol, and an alkoxy oligomer. For oligomers too, one kind or a mixture of two or more kinds of these oligomers may be used.

Further, in the present embodiment, to confer a desired function to the member 100, in addition to the univalent copper compound particles 2, an arbitrarily-used functional material may also be fixed or supported on the substrate 1. Examples of this functional material include another antiviral composition, an antibacterial composition, an antifungal composition, an anti-allergen composition, a catalyst, an anti-reflective material, and a material having a heat blocking property.

Although the amount of the univalent copper compound particles 2 supported in the antiviral member 100 according to the present embodiment may be arbitrarily set in consideration of the purpose and application that the member will be used for and the size of the univalent copper compound particles 2, it is preferred to use 0.1 mass % to 60 mass %, with respect to the total solid content on the substrate 1. If the content of the univalent copper compound particles 2 is less than 0.1 mass %, the antiviral action is less than when the content is in this range. On the other hand, if the content is more than 60 mass %, despite there being no difference in the antiviral activity compared with a content of 60 mass %, the adhesive strength of the group 10 of inorganic particles 3 to the substrate 1 may be less than when the content is in the above range.

In the present embodiment, the group 10 of inorganic particles 3 for supporting the univalent copper compound particles 2 on the surface of the substrate 1 is fixed to the substrate 1. Silane monomers 4 are bonded to the surfaces of the inorganic particles 3 forming this group 10 of inorganic particles by the formation of chemical bonds 8 (covalent bond) formed by a dehydration condensation reaction. The inorganic particles 3 are bonded to each other via chemical bonds 7 (covalent bond) formed between unsaturated bonding sites or reactive functional groups of the silane monomers 4 bonded to the surfaces of the inorganic particles 3.

Further, the group 10 of inorganic particles 3 is fixed to the surface of the substrate 1 by chemical bonds (covalent bond) 5 formed between the silane monomers 4 and the substrate 1. Spaces 9 for supporting the univalent copper compound particles 2 are formed on the substrate 1 by the bonds between the inorganic particles 3 themselves and the bonds between the group 10 of inorganic particles 3 and the substrate 1. The univalent copper compound particles 2 are supported in the spaces 9 in a held state. The spaces 9 are in communication with the outside of the group 10 of inorganic particles 3, so that the univalent copper compound particles 2 are supported on the substrate 1 in a state in which their antiviral activity is maintained.

In other words, in the present embodiment, on the substrate 1 the univalent copper compound particles 2 are surrounded by at least the inorganic particles 3 and the silane monomers 4 that are bonded to the inorganic particles 3, in a state in which their antiviral activity is maintained.

More specifically, the antiviral member 100 according to the present embodiment utilizes the silane monomers 4 which have significant reactivity because they possess an unsaturated bonding site or a reactive functional group to bond the silanol group of these silane monomers 4 to the surfaces of the inorganic particles 3 by chemical bonds 8 (covalent bond) formed by a dehydration condensation reaction.

Further, the inorganic particles 3 are bonded to each other by chemical bonds (covalent bond) 7 formed by radical polymerization between the silane monomers 4 bonded to the surfaces of the inorganic particles 3.

In addition, for example, the group 10 of inorganic particles 3 is fixed to the substrate 1 by chemical bonds (covalent bond) 5 formed by graft polymerization between the surface of the substrate 1, such as a fiber, a film, or a sheet, and the unsaturated bonding site or reactive functional group of the silane monomers 4.

Thus, the group 10 of inorganic particles 3 is strongly fixed to the substrate 1 by the chemical bonds. Consequently, the falling off of the univalent copper compound particles 2, which are supported in the spaces 9 that are formed on the substrate 1 due to the bonds among the inorganic particles 3 themselves and the bonds between the group 10 of inorganic particles 3 and the substrate 1, from the substrate 1 is much more suppressed than conventional cases, in which the fixing is achieved by covering the particles with a component such as a binder. Therefore, the antiviral member 100 according to the present embodiment can maintain an antiviral activity longer than conventional cases.

Further, the univalent copper compound particles 2 can be supported on the substrate 1 in a state in which a binder component and the like is not bonded thereto, or a state in which at least part of the surfaces of the univalent copper compound particles 2 is exposed to the outside. Therefore, the antiviral member 100 according to the present embodiment can exhibit a higher antiviral activity than for a conventional binder fixing method, in which the whole surface of the antiviral component is covered with a binder.

In addition, bumps (bumps smaller than dust) are formed on the surface of the member 100 by the group 10 of inorganic particles 3 fixed to the substrate 1, which suppresses the adhesion of dust and the like. Consequently, since the covering of the surface of the member 100 by dust and the like can be suppressed, antiviral activity can be maintained for a much longer duration than conventional cases.

The inorganic particles 3 may be univalent copper compound particles, or may be inorganic compound particles different from such univalent copper compound particles. Specifically, the inorganic particles 3 may be formed from a non-metal oxide, a metal oxide, a metal composite oxide, or a mixture thereof.

Further, the inorganic particles 3 may be amorphous or crystalline. Examples of a non-metal oxide include silicon oxide. Examples of a metal oxide include magnesium oxide, barium oxide, barium peroxide, aluminum oxide, tin oxide, titanium oxide, zinc oxide, titanium peroxide, zirconium oxide, iron oxide, iron hydroxide, tungsten oxide, bismuth oxide, and indium oxide. Examples of a metal composite oxide include barium titanium oxide, cobalt aluminum oxide, lead zirconium oxide, niobium oxide lead, $TiO_2$—$WO_3$, $AlO_3$—$SiO_2$, $WO_3$—$ZrO_2$, and $WO_3$—$SnO_2$.

Although the particle size (volume average particle size) of the inorganic particles 3 may be arbitrarily set in consideration of the application of the member and the particle size of the univalent copper compound particles 2, in consideration of the bonding strength to the substrate 1, it is preferred to set the particle size to 300 nm or less, and much more preferably to 100 nm or less.

Examples of the silane monomers 4 bonded to the surface of the inorganic particles 3 include silane monomers having an unsaturated bonding site or a reactive functional group, such as a vinyl group, an epoxy group, a styryl group, a methacryloyl group, an acryloxy group, an isocyanate group, and a thiol group.

Specifically, examples include vinyltrimethoxysilane, vinyltriethoxysilane, vinyltriacetoxysilane, N-β-(N-vinylbenzylaminoethyl)-γ-aminopropyltrimethoxysilane, N-(vinylbenzyl)-2-aminoethyl-3-aminopropyltrimethoxysilane hydrochloride, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, 3-isocyanatepropyltriethoxysilane, and an alkoxy silane compound represented by $Si(OR1)_4$ (wherein R1 represents an alkyl group having 1 to 4 carbon atoms), for example, tetramethoxysilane and tetraethoxysilane, and an alkoxy silane compound represented by $R2_xSi(OR3)_n$ (wherein R2 represents a hydrocarbon group having 1 to 6 carbon atoms, R3 represents an alkyl group having 1 to 4 carbon atoms, X is (4−n), and n denotes an integer of 1 to 3), for example, methyltrimethoxysilane, methyltriethoxysilane, dimethyldiethoxysilane, phenyltriethoxysilane, hexyltrimethoxysilane, and hexamethyldisilazane.

The viruses that can be inactivated by the antiviral member 100 according to the present embodiment are not especially limited. Various viruses can be inactivated, regardless of the genome type or the presence of an envelope.

Examples include rhinovirus, poliovirus, rotavirus, norovirus, enterovirus, heptovirus, astrovirus, sapovirus, hepatitis E virus, influenza A, B, and C virus, parainfluenza virus, mumps virus (contagious parotitis), measles virus, human metapneumovirus virus, RS virus, Nipah virus, Hendra virus, yellow fever virus, dengue virus, Japanese encephalitis virus, West Nile virus, hepatitis B and C virus, Eastern and Western equine encephalitis virus, O'nyong'nyong virus, rubellavirus, Lassayirus, Junin virus, Machupo virus, Guanarito virus, Sabia virus, Crimean-Congo hemorrhagic fever virus, sandfly fever, hantavirus, Sin Nombre virus, rabies virus, Ebola virus, Marburg virus, bat Lyssavirus, human T cell leukemia virus, human immunodeficiency virus, human coronavirus, SARS coronavirus, human parvovirus, polyomavirus, human papilloma virus, adenovirus, herpes virus, varicella zoster virus, EB virus, cytomegalovirus, smallpox virus, monkeypox virus, cowpox virus, molluscipoxvirus, and parapoxvirus.

In the antiviral member 100 according to the present embodiment, the substrate 1 may be, for example, a fibrous structure, a film, a sheet, or a molded body such as a panel, so that the univalent copper compound particles 2 can be supported on a variety of surfaces.

The substrate 1 of the antiviral member 100 according to the present embodiment may be an arbitrary substrate, as long as chemical bonds 5 with the silane monomers 4 on the inorganic particles 3 can be formed with the surface of the substrate 1. Examples of such a substrate 1 include a substrate whose surface, at the least, is formed from various types of resin, synthetic fiber, natural fibers such as cotton, hemp, silk, and Japanese paper obtained from a natural fiber.

If the surface or the whole of the substrate 1 is formed from a resin, a synthetic resin or a natural resin may be used.

Examples thereof include thermoplastic resins such as polyethylene resin, polypropylene resin, polystyrene resin, ABS resin, AS resin, EVA resin, polymethylpentene resin, polyvinyl chloride resin, polyvinylidene chloride resin, polymethylacrylate resin, polyvinylacetate resin, polyamide resin, polyimide resin, polycarbonate resin, polyethylene terephthalate resin, polybutylene terephthalate resin, polyacetal resin, polyarylate resin, polysulfone resin, polyvinylidene fluoride resin, Vectran®, and PTFE, biodegradable resins such as polylactic acid resin, polyhydroxybutyrate resin, modified starch resin, polycaprolacto resin, polybutylene succinate resin, polybutylene adipate terephthalate resin, polybutylene succinate terephthalate resin, and polyethylene succinate terephthalate resin, thermosetting resins such as phenol resin, urea resin, melamine resin, unsaturated polyester resin, diallyl phthalate resin, epoxy resin, epoxy acrylate resin, silicon resin, acrylic urethane resin, and urethane resin, elastomers such as silicone resin, polystyrene elastomer, polyethylene elastomer, polypropylene elastomer, and polyurethane elastomer, and natural resins such as Japanese lacquar.

Further, even if the substrate 1 is formed from a metal material such as aluminum, stainless steel, or iron, or an inorganic material such as glass or ceramic, similar to the case of a resin substrate, the group 10 of inorganic particles 3 can be fixed to the metal substrate 1 by, for example, forming the chemical bonds 5 by reacting the unsaturated bonding site or reactive functional group of the silane monomers 4 with a hydroxyl group or the like on the metal surface by the below-described graft polymerization.

On the other hand, the group 10 of inorganic particles 3 can also be strongly fixed by introducing a functional group that can chemically bond to the surface of the substrate 1 with, for example, a silane monomer or a titanium monomer.

Examples of a functional group derived from a silane monomer introduced onto the surface of the substrate 1 include a vinyl group, an epoxy group, a styryl group, a methacryloyl group, an acryloxy group, an isocyanate group, and a thiol group.

The substrate 1 of the antiviral member 100 according to the present embodiment will now be described in more detail.

Examples of the fibrous structure, which is an example of the substrate 1 according to the present embodiment, include woven and nonwoven fabrics. Specific applied examples thereof include masks, air-conditioner filters, air purifier filters, vacuum cleaner filters, ventilation fan filters, automotive filters, air-conditioner filters, clothing, bedding, screen door nets, poultry house nets, and mosquito nets.

The fibrous structure of such examples is formed from fibers of a polymeric material such as polyester, polyethylene, polypropylene, polyvinyl chloride, polyethylene terephthalate, polybutylene terephthalate, polytetramethylene terephthalate, nylon, acrylic, polytetrafluoroethylene, polyvinyl alcohol, Kevlar, polyacrylic acid, polymethyl methacrylate, rayon, cupra, Tencel, polynosic, acetate, triacetate, cotton, hemp, wool, silk, and bamboo, or a metal material such as aluminum, iron, stainless steel, brass, copper, tungsten, and titanium.

Further, the substrate 1 of the antiviral member 100 according to the present embodiment can also be a film or a sheet. If the substrate 1 is a film, it can be formed from, for example, a resin such as polyester, polyethylene, polyamide, polyvinyl chloride, polyvinylidene fluoride, polyvinyl alcohol, polyvinyl acetate, polyimide, polyamideimide, polytetrafluoroethylene, and a tetrafluoroethylene-ethylene copolymer. If the substrate 1 is a sheet, examples thereof include, a sheet formed from a polymer such as polycarbonate sheet/film, vinyl chloride sheet, fluororesin sheet, polyethylene sheet, silicone resin sheet, nylon sheet, ABS sheet, and urethane sheet, and a sheet made of a metal such as titanium, aluminum, stainless steel, magnesium, and brass.

If the substrate 1 is such a film or sheet, to increase the adhesion to the substrate 1 of the group 10 of inorganic particles 3 for supporting the univalent copper compound particles 2, it is preferred to hydrophilize the substrate in advance by subjecting the surface of the substrate to a corona treatment, an atmospheric plasma treatment, a flame treatment and the like. Further, for a sheet made of a metal, it is preferred to remove rolling oil, corrosion product and the like adhered to the surface with, for example, a solvent, an acid, or an alkali. In addition, the sheet surface may also be subjected to painting, printing and the like.

The sheet or film on which the univalent copper compound particles 2 having an antiviral activity are supported can be utilized in various fields, for example, wallpapers, windows, blinds, interior materials used in buildings such as a hospital, interior materials in a train, automobile and the like, automotive sheets, blinds, chairs, sofas, equipment used in handling viruses, and construction materials such as doors, ceiling panels, floor boards, and windows.

Moreover, the antiviral member 100 according to the present embodiment can also be used as a molded body, such as a panel, an interior material, and a construction material. An example thereof may include a molded body formed from a polymer such as ABS, polycarbonate, nylon, polypropylene, polystyrene, polyacetal, and polyester, or a metal such as aluminum, zinc, magnesium, brass, stainless steel, and titanium.

The metal surface may be coated with a thin metal film in advance by electroplating or electroless plating, or be subjected to painting or printing. If the univalent copper compound particles 2 are fixed to a surface of a writing instrument, a handrail, a handstrap, a telephone, a toy, a door knob and the like, the situation in which a healthy person becomes infected with a virus after touching a product or a part that was used by an infected person can be prevented.

Production of the antiviral member 100 according to the present embodiment which includes copper(I) chloride as an example of the univalent copper compound particles 2 will now be described in more detail. In this production, a slurry in which inorganic particles 3, which have silane monomers 4 having an unsaturated bonding site or a reactive functional group chemically bonded to a surface thereof, and copper(I) chloride are dispersed is coated on the substrate 1. Then, the silane monomers 4 chemically bonded to the surface of the inorganic particles 3 are made to bond to each other by a chemical bond, to thereby form a group 10 of inorganic particles 3 bonded via the silane monomers 4.

In conjunction with this, the group 10 of inorganic particles 3, which have silane monomers 4 chemically bonded to a surface thereof, is bonded to the substrate 1. This bond between the group 10 of inorganic particles 3 and the substrate 1 is formulated by chemical bonds between an unsaturated bonding site or a reactive functional group of the silane monomers 4 and the surface of the substrate 1. As a result, spaces 9 for supporting copper (I) chloride are formed, and the copper(I) chloride is supported in the spaces 9.

The copper(I) chloride is pulverized into micron-sized particles by a jet mill, a hammer mill, a ball mill, a vibration mill and the like.

Next, the pulverized copper(I) chloride is mixed with the binder component 6 and the inorganic particles 3 to which the silane monomers 4 having an unsaturated bonding site or a reactive functional group were bonded by dehydration condensation. Then, the resultant mixture is dispersed in a solvent such as water, methanol, ethanol, MEK, acetone, xylene, and toluene. During this process, in addition to the inorganic particles 3 and the copper(I) chloride, another material, for example, the binder component 6 and a functional material may also be admixed. Next, a dispersant such as a surfactant is optionally added, and the resultant mixture is dispersed and crushed using an apparatus such as beads mill, ball mill, sand mill, roll mill, vibration mill, or homogenizer, to produce a slurry in which particles of copper(I) chloride are dispersed.

Consequently, the particle size of the univalent copper compound particles 2 and the inorganic particles 3 is reduced, so that the univalent copper compound particles 2 and the inorganic particles 3 are arranged on the surface of the substrate 1 without excess gaps between these particles. Accordingly, the particle density of the univalent copper compound particles 2 can be increased and the group 10 of inorganic particles 3 can be more strongly fixed to the substrate 1.

Therefore, a high antiviral activity can be exhibited, and antiviral activity can be exhibited for a longer duration than conventionally. The chemical bond (covalent bond) 8 between the inorganic particles 3 and the silane monomers 4 having an unsaturated bonding site or a reactive functional group can be formed by a dehydration condensation reaction based on an ordinary method.

The chemical bond (covalent bond) 8 between the inorganic particles 3 and the silane monomers 4 having an unsaturated bonding site or a reactive functional group can be formed by an ordinary method.

For example, the silane monomers 4 may be added into a dispersion of the inorganic particles 3, then while heating under reflux, made to form covalent bonds 8 with the surfaces of the inorganic particles 3 by a dehydration condensation reaction, whereby a thin film composed of the silane monomers 3 is formed.

Further, as another method, first, the silane monomers 4 may be added into a dispersion of inorganic particles 3 that were pulverized into particles. Alternatively, the inorganic particles 3 can be prepared by adding particles of an inorganic compound for producing the inorganic particles 3 and the silane monomers 4 into a dispersion medium, and then pulverizing the particles of the inorganic compound into the inorganic particles 3. Next, solid-liquid separation is carried out, and the resultant product is heated at 100° C. to 180° C., so that the silane monomers 4 are made to form covalent bonds 8 with the surfaces of the inorganic particles 3 by a dehydration condensation reaction. Lastly, the inorganic particles 3 to which silane monomers 4 are bonded are further pulverized and crushed, and again dispersed.

If the inorganic particles 3 and the silane monomers 4 are covalently bonded by the method described above as an example, although it also depends on the average particle size of the inorganic particles 3, the amount of silane monomers 4 is from 0.01 mass % to 40.0 mass % with respect to the mass of the inorganic particles 3. In this case, in practice there are no problems with the bonding strength among the inorganic particles 3 themselves or between the group 10 of inorganic particles 3 and the substrate 1. Further, it is acceptable for there to be excess silane monomers 4 not participating in the binding.

Subsequently, the thus-produced slurry is coated onto the fibers, film, or sheet surface by a method such as dipping, spraying, roll coating, bar coating, spin coating, gravure printing, offset printing, screen printing, and inkjet printing. Then, optionally, the solvent is removed by heating and drying, for example.

Next, the unsaturated bonding site or reactive functional group of the silane monomers 4 bonded to the surface of the inorganic particles 3 facing the surface of the substrate 1 are made to form covalent bonds 5 with a functional group on the surface of the substrate 1 by graft polymerization induced by reheating or by graft polymerization induced by irradiation such as infrared rays, ultraviolet rays, an electron beam, or γ rays (radiation-induced graft polymerization). Of these, in the present embodiment it is preferred to use radiation-induced graft polymerization.

Further, due to the reheating or the infrared rays, ultraviolet rays, electron beam, or grays from during this graft polymerization, the inorganic particles 3 also bond to each other due to the formation of chemical bonds (covalent bond) 7 by radical polymerization of the unsaturated bonding site or reactive functional group of the silane monomers 4 with the surfaces of the particles.

More specifically, due to radical polymerization induced by reheating or by radical polymerization induced by irradiation such as infrared rays, ultraviolet rays, an electron beam, or γ rays (radiation-induced radical polymerization), chemical bonds (covalent bonds) 7 are formed among the silane monomers. Of these, in the present embodiment it is preferred to use radiation-induced radical polymerization.

Accordingly, the spaces 9 for supporting copper(I) chloride on the substrate 1 are formed, and the copper (I) chloride is supported in a held state in the spaces 9. Further, also in the case where the binder component 6 is added, the binder component 6 may be made to bond to the univalent copper compound particles 2 and the inorganic particles 3 by dehydration condensation due to, for example, the reheating or the infrared rays, ultraviolet rays, electron beam, or γ rays during the graft polymerization.

Based on the above steps, the antiviral member 100 according to the present embodiment in which the univalent copper compound particles 2 having an antiviral activity are supported on the surface of various substrates 1 can be produced.

Although a specific embodiment regarding the present invention was described above, various modifications can be made to the present invention as appropriate within the scope of the above-described technical matter.

For example, the thickness of the group 10 of inorganic particles 3 (in other words, the amount of univalent copper compound particles 2 and inorganic particles 3 supported or fixed on the substrate 1) and the like can be arbitrarily set according to the application of the member 100.

Further, although the group 10 of inorganic particles 3 may be fixed over the whole of the substrate 1 in a layered manner, the present invention is not limited to this.

For example, the group 10 of inorganic particles 3 may be fixed in a non-continuous manner, such as in lines or a sea-island shape over a part or a plurality of regions on the surface of the substrate 1.

EXAMPLES

Next, the present invention will be described in more detail using the following examples. However, the present invention is not limited to only these examples.

Production of Antiviral Member

Examples 1-1 to 1-9

As commercially-available univalent copper compounds, powders (manufactured by Wako Pure Chemical Industries, Ltd., Wako Analytical Grade) of each of copper chloride, copper iodide, copper thiocyanate, and copper oxide were pulverized to an average particle size of about 5 μm by a jet mill. Zirconium oxide grains (manufactured by Nippon Denko Co., Ltd., PCS) having methacryloxypropyltrimethoxysilane (manufactured by Shin-Etsu Chemical Co. Ltd., KBM-503), which is a silane monomer that has an unsaturated bonding site, covalently bonded to a surface thereof by dehydration condensation by an ordinary method and the above univalent copper compounds were dispersed in methanol, then crushed and dispersed using a beads mill to produce a slurry containing the univalent copper compound.

Next, the produced slurry containing the univalent copper compound was sprayed onto 40 g/m² rayon nonwoven fabric (manufactured by Shinwa Corp.), and dried at 100° C. The coated fabric was then irradiated with a 5 Mrad electron beam at an accelerated voltage of 200 kV to obtain an antiviral member. Table 1 shows the ratio (mass %) of the univalent copper compound with respect to the total of the univalent copper compound and the zirconium oxide particles to which the silane monomers having an unsaturated bonding site are bonded, both of which are supported on the surface of the rayon nonwoven fabric. In Table 1, a case in which the slurry does not contain the univalent copper compound is shown as Comparative Example 1. Further, a case that only used phosphate buffered saline (PBS) and did not use a nonwoven fabric is shown as a reference (control).

TABLE 1

|  | Univalent Copper Compound | Content (mass %) |
|---|---|---|
| Example 1-1 | Copper(I) Chloride | 1 |
| Example 1-2 | Copper(I) Chloride | 5 |
| Example 1-3 | Copper(I) Iodide | 5 |

TABLE 1-continued

|  | Univalent Copper Compound | Content (mass %) |
| --- | --- | --- |
| Example 1-4 | Copper(I) Iodide | 20 |
| Example 1-5 | Copper(I) Iodide | 40 |
| Example 1-6 | Copper(I) Thiocyanate | 20 |
| Example 1-7 | Copper(I) Thiocyanate | 40 |
| Example 1-8 | Copper(I) Oxide | 20 |
| Example 1-9 | Copper(I) Oxide | 40 |
| Comparative Example 1 | — | — |
| Reference | (Control) | — |

<Evaluation of Antiviral Activity by Hemagglutination>

The antiviral activity of a nonwoven fabric supporting a univalent copper compound was evaluated by hemagglutination. Used as the target virus was an influenza virus (influenza A/Kita Kyushu/159/93 (H3N2)) grown using NDCK cells. The hemagglutination (HA) titer (HA titer) of the influenza virus brought into contact with respective substances was determined by titration.

Specifically, first, a two-fold dilution series was produced by diluting a sample solution brought into contact with a piece of nonwoven fabric supporting a univalent copper compound with phosphate buffered saline (PBS), and 50 µL of the dilution series was injected into each well of a 96-well round bottomed plate made from plastic. Next, 50 µL of a 0.5 vol % chicken red blood cell suspension was added into each cell. The plate was left at 4° C. for 60 minutes, and then the presence of red blood cell sedimentation was visually observed. At this stage, the maximum dilution factor of the virus solution at which red blood cell sedimentation did not occur was taken as the HA titer.

The sample solutions were acquired in the following manner.

A piece of nonwoven fabric (40 mm×40 mm) on which a univalent copper compound was fixed was finely cut with a cutter, and each of the cut pieces was placed in a vessel. Each vessel was added with 1 mL of PBS and 1 mL of an influenza solution having an HA titer of 256, respectively. Then, while stirring with a microtube rotator, the solutions were reacted at room temperature for 10 minutes or 60 minutes. A control was produced by adding 450 µL of virus solution having an HA titer of 256 into 450 µL of PBS, and then stirring using a microtube rotator for 10 minutes or 60 minutes. The sample solutions for each reaction time were then recovered, and the HA titer was measured.

The measurement results are shown in Table 2.

TABLE 2

|  | HA Titer | |
| --- | --- | --- |
|  | 10 Minutes | 60 Minutes |
| Example 1-1 | <2 | <2 |
| Example 1-2 | <2 | <2 |
| Example 1-3 | 16 | 8 |
| Example 1-4 | 4 | <2 |
| Example 1-5 | <2 | <2 |
| Example 1-6 | 64 | 32 |
| Example 1-7 | 32 | 16 |
| Example 1-8 | 64 | 32 |
| Example 1-9 | 16 | 8 |
| Comparative Example 1 | 126 | 126 |
| Reference | 126 | 126 |

Production of Antiviral Member

Example 2

A commercially-available copper(I) chloride powder (manufactured by Wako Pure Chemical Industries, Ltd., Wako Analytical Grade) pulverized to an average particle size of 5 µm by a jet mill and zirconium oxide grains (manufactured by Nippon Denko Co., Ltd., PCS) having methacryloxypropyltrimethoxysilane (manufactured by Shin-Etsu Chemical Co. Ltd., KBM-503), which is a silane monomer that has an unsaturated bonding site, covalently bonded to the surface by dehydration condensation by an ordinary method were dispersed in methanol, then crushed and dispersed using a bead mill to produce a slurry containing particles of both the copper(I) chloride having an average particle size of 60 nm and the zirconium oxide having an average particle size of 37 nm and having methacryloxypropyltrimethoxysilane bonded to the surface. Methanol was added into the obtained slurry to adjust its solid content concentration to 5 mass %. Here, the term "average particle size" refers to volume average particle size.

The filled amount of the copper(I) chloride particles was adjusted so that the solid content, specifically, the copper(I) chloride particles, on the substrate after the substrate surface was dried to remove the solvent was 0.1 mass % (Example 2-1) or 1.0 mass % (Example 2-2) with respect to the total of the zirconium oxide particles having methacryloxypropyltrimethoxysilane bonded thereto and the copper(I) chloride particles.

Next, the surface of a 125 µm-thick polyester film (manufactured by Toray Industries, Lumira) was hydrophilized by a corona treatment. The slurry was then coated thereon with a bar coater, and dried at 100° C. for 5 minutes. The coated member was then irradiated with a 5 Mrad electron beam at an accelerated voltage of 200 kV to obtain an antiviral member.

Example 3

The antiviral members of Examples 3-1 and 3-2 were obtained under the same conditions as in Example 2, except that nonwoven fabric made from nylon (Asahi Kasei Fibers Corporation, 1020) was used instead of the polyester film used in Example 2, and the nonwoven fabric was coated with a slurry by dipping in the slurry used in Example 2.

Example 4

The antiviral member of Example 4 was obtained by the same method as Example 2, except that the filled amount of the copper(I) chloride particles was adjusted so that the solid content, specifically, the copper(I) chloride particles, on the substrate after the substrate surface was dried to remove the solvent was 0.05 mass % with respect to the total of the zirconium oxide particles having methacryloxypropyltrimethoxysilane bonded thereto and the copper(I) chloride particles.

Example 5

The antiviral members of Example 5 were obtained by the same method as Example 2, except that copper (I) iodide was used instead of the copper(I) chloride used in Example 2, and that the solid content, specifically, the copper(I) iodide particles, on the substrate was adjusted to 20 mass % (Example 5-1) or 40 mass % (Example 5-2) with respect to the total of the zirconium oxide particles having methacryloxypropyltrimethoxysilane bonded thereto and the copper(I) iodide particles.

Example 6

The antiviral member of Example 6 was obtained by the same method as Example 3, except that copper(I) thiocyanate was used instead of the copper chloride used in Example 3, and that the solid content, specifically, the copper(I) thiocyanate, on the substrate was adjusted to 40 mass % with respect to the total of the zirconium oxide particles having methacryloxypropyltrimethoxysilane bonded thereto and the copper(I) thiocyanate particles.

Example 7

The antiviral member of Example 7 was obtained by the same method as Example 3, except that copper(I) oxide was used instead of the copper(I) chloride used in Example 3, and that the solid content, specifically, the copper(I) oxide, on the substrate was adjusted to 40 mass % with respect to the total of the zirconium oxide particles having methacryloxypropyltrimethoxysilane bonded thereto and the copper(I) oxide particles.

Comparative Example 2

The polyester film used in Example 2 was subjected to a corona treatment under the same conditions as Example 2, and used for evaluation of antiviral activity.

Comparative Example 3

A slurry was produced by crushing and dispersing the zirconium oxide grains having methacryloxypropyltrimethoxysilane (manufactured by Shin-Etsu Chemical Co. Ltd., KBM-503) bonded to a surface thereof used in Example 2 using a bead mill under the same conditions as in Example 2, and adding methanol to adjust the solid content to 5 mass %. The produced slurry was coated onto a polyester film surface under the same conditions as Example 2 to form a thin film of zirconia that did not contain copper(I) chloride particles. This thin film was used in evaluation of antiviral activity.

(Evaluation of Antiviral Activity According to the Present Invention)

Antiviral activity was evaluated in terms of antiviral activity against feline calicivirus which is generally used as a substitute for norovirus.

Each sample (circular shape with a 10 cm diameter) was placed in a sterilized petri dish. The whole periphery of the sample was fixed to the bottom of the petri dish with an adhesive. For the examples in which the sample was a film (Examples 2, 4, and 5, and Comparative Examples 2 and 3), 6 mL of feline calicivirus solution was added, and for the examples in which the sample was a piece of nonwoven fabric (Examples 3, 6, and 7), 12 mL of feline calicivirus solution was added. The dishes were then shaken at 200 rpm/minute in a 25° C. dark place.

Next, 100 µL of test solution was collected, and 1800 µL of 20 mg/mL nutrient broth was added to terminate the reaction. Then, each reaction sample was diluted with an MEM diluent to $10^{-2}$ to $10^{-5}$ (10-fold serial dilution), and confluent CrFK cells were inoculated with 100 µL of the post-reaction sample solution. After 90 minutes of virus adsorption, a 0.7% agar medium was laid over the cell. The virus was grown for 48 hours in a 34° C., 5% $CO_2$ incubator, fixed in formalin, and stained with methylene blue. The infectivity titer (PFU/0.1 mL, Log 10); (PFU: plaque forming units) of the virus was calculated by counting the number of formed plaques. Virus activity was compared by comparing with the viral infectivity in the control.

(Control)

A control was produced using an MEM diluent to which a sample had not been added.

TABLE 3

|  | Univalent Copper Compound | Concentration (mass %) | Contact Time (minutes) | Viral Infectivity (PFU/ 0.1 ml, Log10) |
|---|---|---|---|---|
| Example 2-1 | Copper(I) Chloride | 0.1 | 5 | <1 |
| Example 2-2 | Copper(I) Chloride | 1.0 | 5 | <1 |
| Example 3-1 | Copper(I) Chloride | 0.1 | 5 | <1 |
| Example 3-2 | Copper(I) Chloride | 1.0 | 5 | <1 |
| Example 4 | Copper(I) Chloride | 0.05 | 5 | 3.08 |
| Example 5-1 | Copper(I) Iodide | 20.0 | 30 | <1 |
|  | Copper(I) Iodide | 20.0 | 60 | <1 |
| Example 5-2 | Copper(I) Iodide | 40.0 | 5 | <1 |
|  | Copper(I) Iodide | 40.0 | 10 | <1 |
| Example 6 | Copper(I) Thiocyanate | 40.0 | 60 | <1 |
| Example 7 | Copper(I) Oxide | 40.0 | 60 | <1 |
| Comparative Example 2 | — | — | 5 | 5.00 |
|  |  |  | 60 | 4.91 |
| Comparative Example 3 | — | — | 5 | 4.87 |
|  |  |  | 60 | 4.78 |
| Control | — | — | 5 | 6.02 |
|  |  |  | 60 | 5.95 |

Based on the above results, a high inactivation rate of 99% or more in a short time was found for all of Examples 2 to 7, which include univalent copper compounds. Especially for Examples 2, 3, 5, 6 and 7 a very high antiviral action of 99.999% or more was found. In contrast, for Comparative Examples 2 and 3, almost no antiviral effect was exhibited.

Here, the term "inactivation rate" refers to a value defined according to the following formula.

$$\text{Inactivation Rate (\%)} = 100 \times (10^a - 10^b)/10^a$$

Wherein:
a: Blank viral infectivity
b: Sample viral infectivity

Thus, it was confirmed that the antiviral member according to the present invention has a very high antiviral action against both the feline calicivirus, which does not have an envelope, and the influenza virus, which has an envelope. Therefore, the inventive antiviral member can be applied in various substrates, such as a fibrous structure, a film, a sheet, or a molded body, so that a highly effective antiviral product can be provided.

DESCRIPTION OF REFERENCE NUMERAL

100 antiviral member
1 substrate
2 univalent copper compound particle
3 inorganic particle 4 silane monomer
5 chemical bond between substrate and silane monomer
6 binder component
7 chemical bond between silane monomers
8 chemical bond between inorganic particle and silane monomer by dehydration condensation
9 space for supporting univalent copper compound particle
10 group of inorganic particles

The invention claimed is:

1. An antiviral member, comprising:
a substrate;
univalent copper compound particles; and
a group of inorganic particles which are for supporting the univalent copper compound particles on the substrate and which have a silane monomer chemically bonded to a surface thereof, wherein
the inorganic particles having the silane monomer on the surface thereof are bonded to each other via chemical bonds formed between the silane monomers provided on the surface of the inorganic particles, and the group of inorganic particles are bonded to the substrate due to the chemical bonds between the silane monomers on the surface of the inorganic particles and the substrate,
whereby the group of inorganic particles forms spaces for supporting the univalent copper compound particles.

2. An antiviral member, made by:
coating a substrate with a slurry in which inorganic particles having a silane monomer, which has an unsaturated bonding site or a reactive functional group, chemically bonded to a surface thereof and univalent copper compound particles are dispersed,
making the inorganic particles having the silane monomer chemically bonded to the surface thereof be bonded to each other by chemical bonds that are formed between the silane monomers on the surface of the inorganic particles, and making the group of inorganic particles having the silane monomer chemically bonded to the surface thereof be bonded to the substrate by chemical bonds formed between the unsaturated bonding site or the reactive functional group of the silane monomers and the substrate surface, whereby spaces for supporting the univalent copper compound particles is formed, and
supporting the univalent copper compound particles in the space.

3. The antiviral member according to claim 1, wherein:
the chemical bonds between the silane monomers and the inorganic particles are covalent bonds formed by dehydration condensation, the chemical bonds among the silane monomers are covalent bonds formed by radical polymerization, and
the chemical bonds between the silane monomers and the substrate are covalent bonds formed by graft polymerization.

4. The antiviral member according to claim 3, wherein the radical polymerization is radiation-induced radical polymerization, and the graft polymerization is radiation-induced graft polymerization.

5. The antiviral member according to claim 1, wherein the univalent copper compound particles are bonded to the inorganic particles via a binder component which is a monomer, an oligomer, or a mixture thereof.

6. The antiviral member according to claim 1, wherein the univalent copper compound particles are formed of a chloride, an acetate, a sulfide, an iodide, a bromide, a peroxide, an oxide, a hydroxide, a cyanide, a thiocyanate or a mixture thereof.

7. The antiviral member according to claim 1, wherein the univalent copper compound particles are formed of at least one kind selected from the group consisting of CuCl, $CuCH_3COO$, CuI, CuBr, $Cu_2O$, CuOH, $Cu_2S$, CuCN, and CuSCN.

8. The antiviral member according to claim 1, wherein a content of the univalent copper compound particles is, with respect to a total solid content on the substrate, 0.1 mass % to 60 mass %.

9. The antiviral member according to claim 1, wherein the substrate is a fibrous structure.

10. The antiviral member according to claim 2, wherein:
the chemical bonds between the silane monomers and the inorganic particles are covalent bonds formed by dehydration condensation, the chemical bonds among the silane monomers are covalent bonds formed by radical polymerization, and
the chemical bonds between the silane monomers and the substrate are covalent bonds formed by graft polymerization.

11. The antiviral member according to claim 10, wherein the radical polymerization is radiation-induced radical polymerization, and the graft polymerization is radiation-induced graft polymerization.

12. The antiviral member according to claim 2, wherein the univalent copper compound particles are bonded to the inorganic particles via a binder component which is a monomer, an oligomer, or a mixture thereof.

13. The antiviral member according to claim 2, wherein the univalent copper compound particles are formed of a chloride, an acetate, a sulfide, an iodide, a bromide, a peroxide, an oxide, a hydroxide, a cyanide, a thiocyanate or a mixture thereof.

14. The antiviral member according to claim 2, wherein the univalent copper compound particles are formed of at least one kind selected from the group consisting of CuCl, $CuCH_3COO$, CuI, CuBr, $Cu_2O$, CuOH, $Cu_2S$, CuCN, and CuSCN.

15. The antiviral member according to claim 2, wherein a content of the univalent copper compound particles is, with respect to a total solid content on the substrate, 0.1 mass % to 60 mass %.

16. The antiviral member according to claim 2, wherein the substrate is a fibrous structure.

* * * * *